US00PP36774P2

(12) United States Plant Patent
Hattori

(10) Patent No.: US PP36,774 P2
(45) Date of Patent: Jun. 24, 2025

(54) ***HELLEBORUS* PLANT NAMED 'Borusmura40'**

(50) Latin Name: ***Helleborus* x *sternii* (*Helleborus argutifolius* X *Helleborus lividus*)**
Varietal Denomination: Borusmura40

(71) Applicant: Miyoko Hattori, Tokyo (JP)

(72) Inventor: Miyoko Hattori, Tokyo (JP)

( * ) Notice: Subject to any disclaimer, the term of this patent is extended or adjusted under 35 U.S.C. 154(b) by 0 days.

(21) Appl. No.: 18/955,822

(22) Filed: Nov. 21, 2024

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
See application file for complete search history.

(56) References Cited

U.S. PATENT DOCUMENTS

PP21,003 P2 * 5/2010 Heuger ..... A01H 5/02 Plt./439

* cited by examiner

*Primary Examiner* — Susan McCormick Ewoldt
(74) *Attorney, Agent, or Firm* — C. Anne Whealy

(57) ABSTRACT

A new and distinct cultivar of *Helleborus* plant named 'Borusmura40', characterized by its relatively compact, upright to outwardly spreading and mounding plant habit; moderately vigorous growth habit; deeply serrated leaflets that have silvery green-colored upper surfaces that are densely and lower surfaces that are dark purple in color; freely flowering habit; purplish red-colored flowers; and good garden performance.

2 Drawing Sheets

Figure 1:
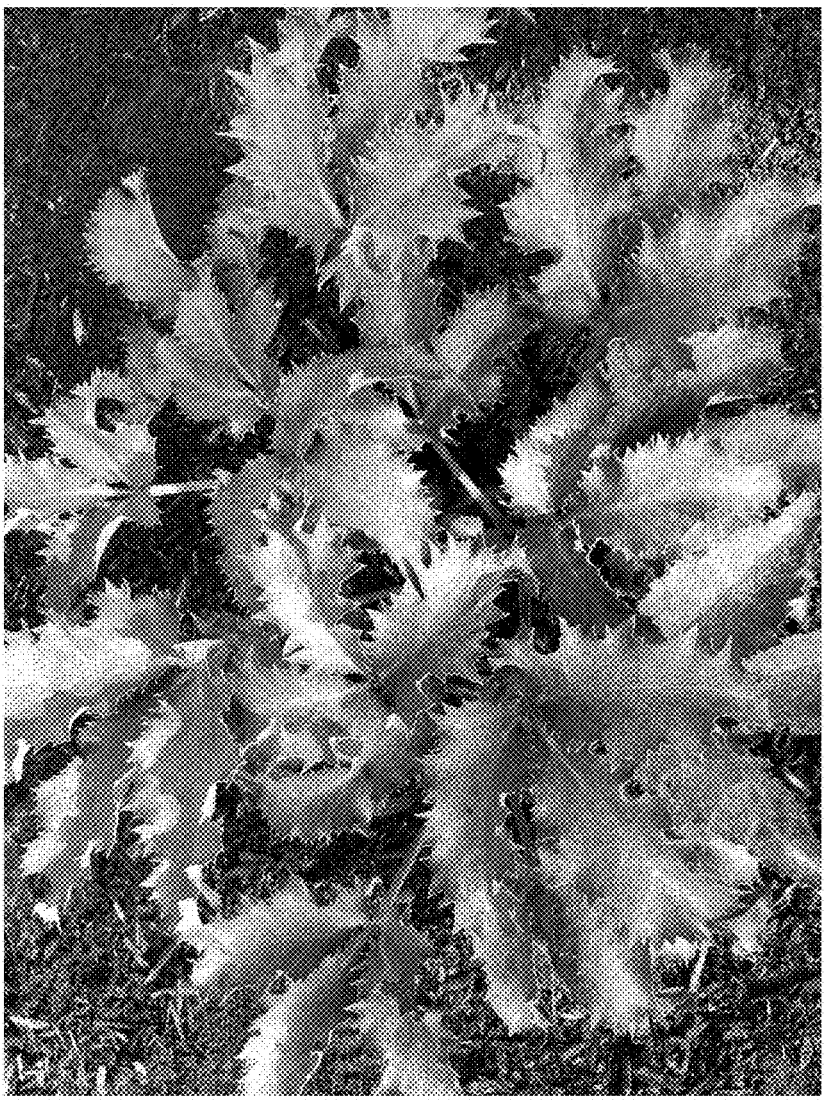

Botanical designation: *Helleborus* x *sternii* (*Helleborus argutifolius* X *Helleborus lividus*).
Cultivar denomination: 'BORUSMURA40'.

BACKGROUND OF THE INVENTION

The present invention relates to a new and distinct cultivar of *Helleborus* plant, botanically known as *Helleborus* x *sternii* (*Helleborus argutifolius* X *Helleborus lividus*), commonly referred to as an interspecific hybrid Hellebore and hereinafter referred to by the name 'Borusmura40'.

The new *Helleborus* plant is a product of a planned breeding program conducted by the Inventor in Kiyose, Japan. The objective of the breeding program was to create new uniformly mounding and freely-flowering *Helleborus* plants with attractive leaves and flowers.

The new *Helleborus* plant originated from a cross-pollination conducted by the Inventor in Toyko, Japan in March 2016 of an unidentified proprietary selection of *Helleborus argutifolius*, not patented, as the female, or seed, parent with an unidentified proprietary selection of *Helleborus lividus*, not patented, as the male, or pollen, parent. The new *Helleborus* plant was discovered and selected by the Inventor as a single flowering plant from within the progeny of the stated cross-pollination grown in a controlled greenhouse environment in Kiyose, Japan in March 2018.

Asexual reproduction of the new *Helleborus* plant by divisions in a controlled greenhouse environment in Kiyose, Japan since March 2018, has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype of the new *Helleborus* plant may vary somewhat with variations in environmental conditions such as temperature and light intensity without, however, any variance in genotype of the new *Helleborus* plant.

The following traits have been repeatedly observed and are determined to be the unique characteristics of 'Borusmura40'. These characteristics in combination distinguish 'Borusmura40' as a new and distinct *Helleborus* plant:

1. Relatively compact, upright to outwardly spreading and mounding plant habit.
2. Moderately vigorous growth habit.
3. Deeply serrated leaflets that have silvery green-colored upper surfaces that are densely and lower surfaces that are dark purple in color.
4. Freely flowering habit.
5. Purplish red-colored flowers.
6. Good garden performance.

Plants of the new *Helleborus* differ primarily from plants of the female parent selection in the following characteristics:

1. Leaflets of plants of the new *Helleborus* have deeply serrated margins whereas leaflets of plants of the female parent selection have non-serrated margins.
2. Leaflets of plants of the new *Helleborus* are silvery green in color whereas leaflets of plants of the female parent selection are greyish green in color.
3. Flowers of plants of the new *Helleborus* are purplish red in color whereas flowers of plants of female parent selection are green in color.

Plants of the new *Helleborus* differ primarily from plants of the male parent selection in the following characteristics:

1. Leaflets of plants of the new *Helleborus* have deeply serrated margins whereas leaflets of plants of the male parent selection have shallowly serrated margins.
2. Leaflets of plants of the new *Helleborus* are silvery green in color whereas leaflets of plants of the male parent selection are green in color with white mottling.
3. Flowers of plants of the new *Helleborus* are purplish red in color whereas flowers of plants of male parent selection are light green in color slightly flushed with purplish red.

Plants of the new *Helleborus* can be compared to plants of *Helleborus niger* X *Helleborus lividus* 'COSEH 700', disclosed in U.S. Plant Pat. No. 21,003. In side-by-side comparisons, plants of the new *Helleborus* differ from plants of 'COSEH 700' in the following characteristics:

1. Leaflets of plants of the new *Helleborus* have more deeply serrated margins than leaflets of plants of 'COSEH 700'.
2. Leaflets of plants of the new *Helleborus* are silvery green in color whereas leaflets of plants of 'COSEH 700' are dark green in color.
3. Flowers of plants of the new *Helleborus* are purplish red in color whereas flowers of plants of 'COSEH 700' are light green in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1) is a top perspective view of a typical non-flowering plant of 'Borusmura40'.

Figure 2:
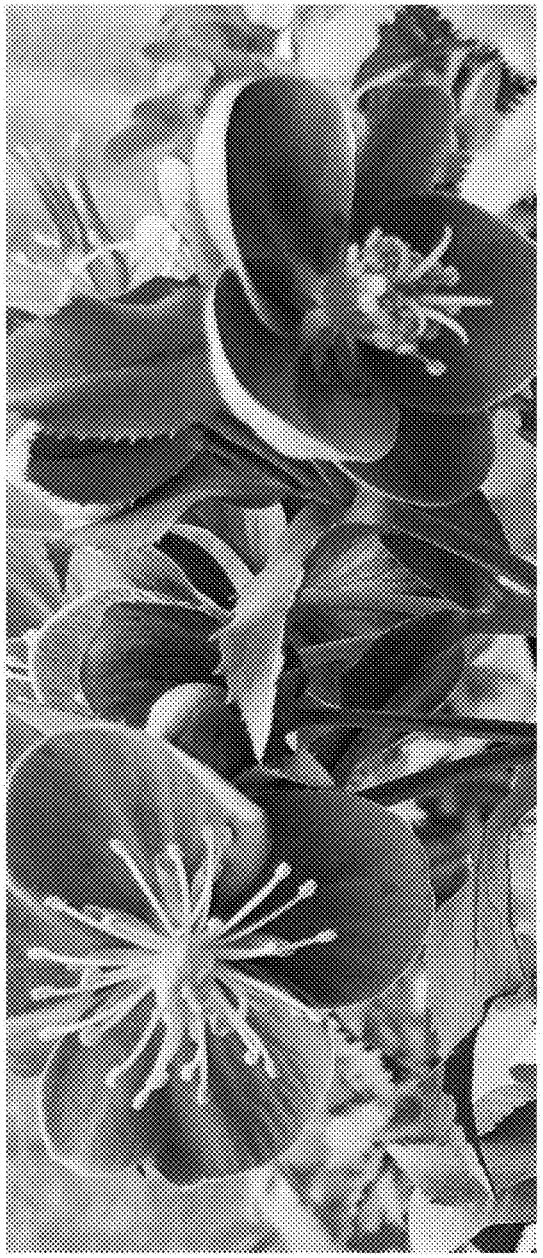

The photograph on the second sheet (FIG. 2) is a close-up view of a typical flowering plant of 'Borusmura40'.

DETAILED BOTANICAL DESCRIPTION

The aforementioned photographs and following observations, measurements and values describe plants grown during the late winter in an outdoor nursery in Smoketown, Pennsylvania and under cultural practices typical of commercial *Helleborus* production. During the production of the plants, day temperatures ranged from 17° C. to 22° C., night temperatures ranged from 5° C. to 10° C. and light levels ranged from 30 to 70 klux. Plants were 1.75 years old when the photographs and the description were taken. In the following description, color references are made to The Royal Horticultural Society Colour Chart, Sixth Edition, except where general terms of ordinary dictionary significance are used.

Botanical classification: *Helleborus* x *sternii* (*Helleborus argutifolius* X *Helleborus lividus*) 'Borusmura40'.

Parentage:

*Female, or seed, parent*.—Unidentified proprietary selection of *Helleborus argutifolius*, not patented.

*Male, or pollen, parent*.—Unidentified proprietary selection of *Helleborus lividus*, not patented.

Propagation:

*Type*.—By in vitro meristem culture.

*Time to initiate roots*.—About three to four weeks at soil temperatures about 20° C. and ambient temperatures about 22° C.

*Time to produce a rooted young plant*.—About six to eight weeks at soil temperatures about 20° C. and ambient temperatures about 22° C.

*Root description*.—Fleshy, medium in thickness; typically white to dark brown in color, actual color of the roots is dependent on substrate composition, water quality, fertilizer type and formulation, substrate temperature and physiological age of roots.

*Rooting habit*.—Moderate branching; medium density.

Plant description:

*Plant and growth habit*.—Herbaceous perennial; relatively compact, upright to outwardly spreading and mounding plant habit; overall plant shape, inverted triangle; moderately vigorous growth habit and moderate growth rate; leaves arranged in basal rosettes.

*Plant height, soil level to top of foliar plane*.—About 14 cm to 20 cm.

*Plant height, soil level to top of floral plane*.—About 14 cm to 20 cm.

*Plant diameter* (*area of spread*).—About 45 cm to 50 cm.

Leaf description:

*Arrangement*.—Leaves arranged alternately in a basal rosette; leaves palmately compound with typically three leaflets per leaf.

*Leaf length*.—About 10 cm to 15 cm.

*Leaf width*.—About 8 cm to 14 cm.

*Leaflet length*.—About 8 cm to 10 cm.

*Leaflet width*.—About 3 cm to 4 cm.

*Leaf shape*.—Compound trifoliate.

*Leaflet shape*.—Lanceolate to narrowly elliptic.

*Leaflet apex*.—Acute.

*Leaflet base*.—Center leaflet, attenuate; lateral leaflets, oblique.

*Leaflet margin*.—Deeply serrate.

*Leaflet texture and luster, upper and lower surfaces*.—Smooth, glabrous; leathery; matte.

*Leaflet venation pattern*.—Pinnate and reticulate.

*Leaflet color*.—Developing leaflets, upper surface: Close to 188B to 188C. Developing leaflets, lower surface: Close to N187C to N187D. Fully expanded leaflets, upper surface: Close to 188A to 188B; midvein, proximally, close to 71A and N79A and distally, close to 141B. Fully expanded leaflets, lower surface: Close to N189C; midvein, close to N77B and N79A.

*Petioles*.—Length, fully expanded leaflets: About 5 cm to 10 cm. Diameter, fully expanded leaflets: About 3 mm to 5 mm. Strength: Strong. Texture and luster, upper and lower surfaces: Smooth, glabrous; matte and waxy. Color, upper and lower surfaces: Close to N79A to N79B.

Flower description:

*Flower shape and habit*.—Single rotate cyanthiform flowers arranged in terminal and axillary cymes; freely flowering habit with typically about 14 to 18 flowers developing per cyme and about 60 to 80 flowers developing during the flowering season; flowers face outwardly to drooping.

*Fragrance*.—None detected.

*Natural flowering season*.—Plants flower continuously throughout February and March in Pennsylvania.

*Flower longevity on the plant*.—About three weeks; sepals are persistent and other flower parts are not persistent.

*Flower buds*.—Length: About 1.5 cm to 2 cm. Diameter: About 1 cm to 1.5 cm. Shape: Ovoid. Texture and luster: Smooth, glabrous; matte. Color: Close to N77B; towards the base, close to 138D.

*Inflorescence height*.—About 16 cm to 20 cm.

*Inflorescence diameter*.—About 8 cm to 10 cm.

*Flower diameter*.—About 5 cm to 6 cm.

*Flower depth* (*height*).—About 2 cm to 3 cm.

*Petals*.—None observed; transformed into nectaries.

*Sepals*.—Quantity and arrangement: About four or five arranged in a single whorl. Length: About 2.5 cm to 3 cm. Width: About 1.5 cm to 2 cm. Shape: Oval. Apex: Obtuse. Base: Acute. Margin: Finely serrate. Texture and luster, upper and lower surfaces: Smooth, glabrous; matte. Color: When opening, upper surface: Close to N77C; marginal edges, close to NN155B. When opening, lower surface: Close to N77D; marginal edges, close to NN155B. Fully opened, upper surface: Close to N77B and N77C; fine marginal edges, close to NN155B. Fully opened, lower surface: Close to N77C; fine marginal edges, close to NN155B.

*Peduncles*.—Length: About 2 cm to 3 cm. Diameter: About 2 mm by 4 mm. Strength: Moderately strong to strong. Aspect: About 15° to 20° from plant axis. Texture and luster: Smooth, glabrous; somewhat glossy. Color: Close to 130D speckled with close to 60B.

*Reproductive organs*.—Stamens: Quantity per flower: About 20 to 40.Filament length: About 1 cm to 1.5 cm. Filament color: Close to 145C. Anther shape: Oblong and retuse; basifixed. Anther size: About 1 mm by 2 mm. Anther color: Close to 150C. Pollen amount: Scarce. Pollen color: Close to 155A Pistils: Quantity per flower: About four to six. Pistil length: About 1.5 cm to 2 cm. Stigma shape: Tapered, pointed. Stigma color: Close to 150C. Style length: About 1 cm to 1.2 cm. Style color: Close to 59A. Ovary color: Close to 145B.

*Nectaries*.—Quantity per flower: About six to ten. Length: About 6 mm to 8 mm. Width: About 1 mm to 2 mm. Shape: Tubular with circular apex. Margin: Entire; slightly undulate. Texture and luster, inner and outer surfaces: Smooth, glaucous; matte to slightly glossy. Color: When opening and fully opened, inner surface: Close to 144C to 144D; color does not change with subsequent development. When opening and fully opened, outer surface: Close to 144C; at the apex, close to 150A; color does not change with subsequent development. Seeds and fruits: To date, seed and fruit development have not been observed on plants of the new *Helleborus*.

Garden performance: Plants of the new *Helleborus* have been observed to have good garden performance and to tolerate rain, wind and temperatures ranging from about −15° C. to about 34° C.

Pathogen & pest resistance: To date, plants of the new *Helleborus* have not been observed to be resistant to pathogens and pests common to *Helleborus* plants.

It is claimed:

1. A new and distinct *Helleborus* plant named 'Borusmura40' as herein illustrated and described.

* * * * *